United States Patent [19]

Czekai et al.

[11] Patent Number: 5,718,388
[45] Date of Patent: Feb. 17, 1998

[54] CONTINUOUS METHOD OF GRINDING PHARMACEUTICAL SUBSTANCES

[75] Inventors: David A. Czekai, Honeoye Falls; Larry P. Seaman, Mount Morris, both of N.Y.

[73] Assignee: Eastman Kodak, Rochester, N.Y.

[21] Appl. No.: 249,787

[22] Filed: May 25, 1994

[51] Int. Cl.$^6$ .................................................. B02C 17/16
[52] U.S. Cl. .................................................. 241/21; 241/24
[58] Field of Search ...................................... 241/5, 21, 22, 241/30, 24, 29, 170–183, 184

[56] References Cited

U.S. PATENT DOCUMENTS

| | | | |
|---|---|---|---|
| 2,595,117 | 4/1952 | Ahlmann | 241/184 X |
| 3,713,593 | 1/1973 | Morris et al. | 241/184 X |
| 4,860,957 | 8/1989 | Lidström | 241/184 X |
| 5,174,512 | 12/1992 | Orlandi | 241/184 X |
| 5,257,742 | 11/1993 | Yashima et al. | 241/184 X |
| 5,320,284 | 6/1994 | Nishida et al. | 241/184 X |

FOREIGN PATENT DOCUMENTS

| | | | |
|---|---|---|---|
| 132162 | 5/1990 | Japan | 241/184 |
| 253512 | 10/1993 | Japan | 241/184 |

*Primary Examiner*—Timothy V. Eley
*Attorney, Agent, or Firm*—Arthur H. Rosenstein

[57] ABSTRACT

A continuous method of preparing submicron particles of a therapeutic or diagnostic agent comprises the steps of continuously introducing the agent and rigid grinding media into a milling chamber, contacting the agent with the grinding media while in the chamber to reduce the particle size of the agent, continuously removing the agent and the grinding media from the milling chamber, and thereafter separating the agent from the grinding media. In a preferred embodiment, the grinding media is a polymeric resin having a mean particle size of less than 300 μm. In another preferred embodiment, the agent, grinding media and a liquid dispersion medium are continuously introduced into the milling chamber. In a further embodiment, the agent and grinding media are recirculated through the milling chamber. The method enables the use of fine grinding media, e.g., of a particle size of less than about 300 μm, in a continuous grinding process which provides extremely fine particles of the agent, e.g., particles less than 100 nm in size, while avoiding problems, e.g., separator screen plugging, associated with prior art processes requiring the separation of agent from the grinding media in the milling chamber.

12 Claims, 1 Drawing Sheet

CONTINUOUS METHOD OF GRINDING PHARMACEUTICAL SUBSTANCES

BACKGROUND OF THE INVENTION

Various grinding media, such as stainless steel, zirconium silicate, zirconium oxide, glass, and the like, typically in the form of spherical beads, are commonly used in various mills, including media mills, for grinding materials. Heretofore, efforts have been made to control the size and size range of drug particles in pharmaceutical compositions by a variety of methods, including various milling techniques, such as airjet milling and wet milling.

Conventional mills used for size reduction in a continuous mode incorporate a means for retaining milling media in the milling zone of the mill, i.e., the milling chamber, while allowing the dispersion or slurry to recirculate through the mill to a stirred holding vessel. Various techniques have been established for retaining media in these mills, including rotating gap separators, screens, sieves, centrifugally-assisted screens, and similar devices to physically restrict passage of media from the mill.

Recently, significant efforts have been made toward the use of smaller milling media in conventional media mill processes for the preparation of various paints, and pigment, photographic and pharmaceutical dispersions. This has been possible due to improvements in mill designs which allow the use of media as small as about 300 µm. The advantages of small media include more efficient comminution, e.g., faster rates of size reduction, and smaller ultimate particle sizes. However, even with the best machine designs available, it is generally not possible to use media smaller than about 300 µm due to separator screen plugging and unacceptable pressure build-up due to hydraulic packing of the media. In fact, for commercial applications, a grinding media size of 350 µm is considered the practical lower limit due to media separator screen limitations.

SUMMARY OF THE INVENTION

We have discovered a continuous grinding process for preparing extremely fine particles which avoids various problems, e.g., separator screen plugging and unacceptable pressure build up due to hydraulic packing of the media, associated with prior art processes requiring the separation of the dispersion agent from the grinding media in the milling chamber.

More specifically, in accordance with this invention, there is provided a method of preparing submicron-sized particles of a therapeutic or diagnostic agent which comprises continuously introducing the agent and rigid grinding media into a milling chamber, contacting the agent with the grinding media while in the chamber to reduce the particle size of the agent, continuously removing the agent and the grinding media from the milling chamber, and thereafter separating the agent from the grinding media.

In another embodiment of the invention, the therapeutic or diagnostic agent, grinding media and a liquid dispersion medium are continuously introduced and removed from the milling chamber.

It is a particularly advantageous feature of this invention that there is provided a continuous method of preparing extremely fine particles of therapeutic and diagnostic agents.

It is another advantageous feature of this invention that there is provided a grinding method which enables the use of ultra-fine grinding media, e.g., of a particle size less than 300 µm, in a continuous grinding process.

Still another advantageous feature of this invention is that there is provided a continuous grinding process which avoids problems, e.g., separator screen plugging, associated with prior art processes requiring the separation of the dispersion agent from the grinding media in the milling chamber.

Yet another advantageous feature of this invention is that there is provided a method of fine grinding therapeutic and diagnostic agents, which method generates less heat and reduces potential heat-related problems such as chemical instability and contamination.

Other advantageous features will become readily apparent upon reference to the following description of preferred embodiments when in read in light of the accompanying drawing.

DESCRIPTION OF PREFERRED EMBODIMENTS

Figure 1:
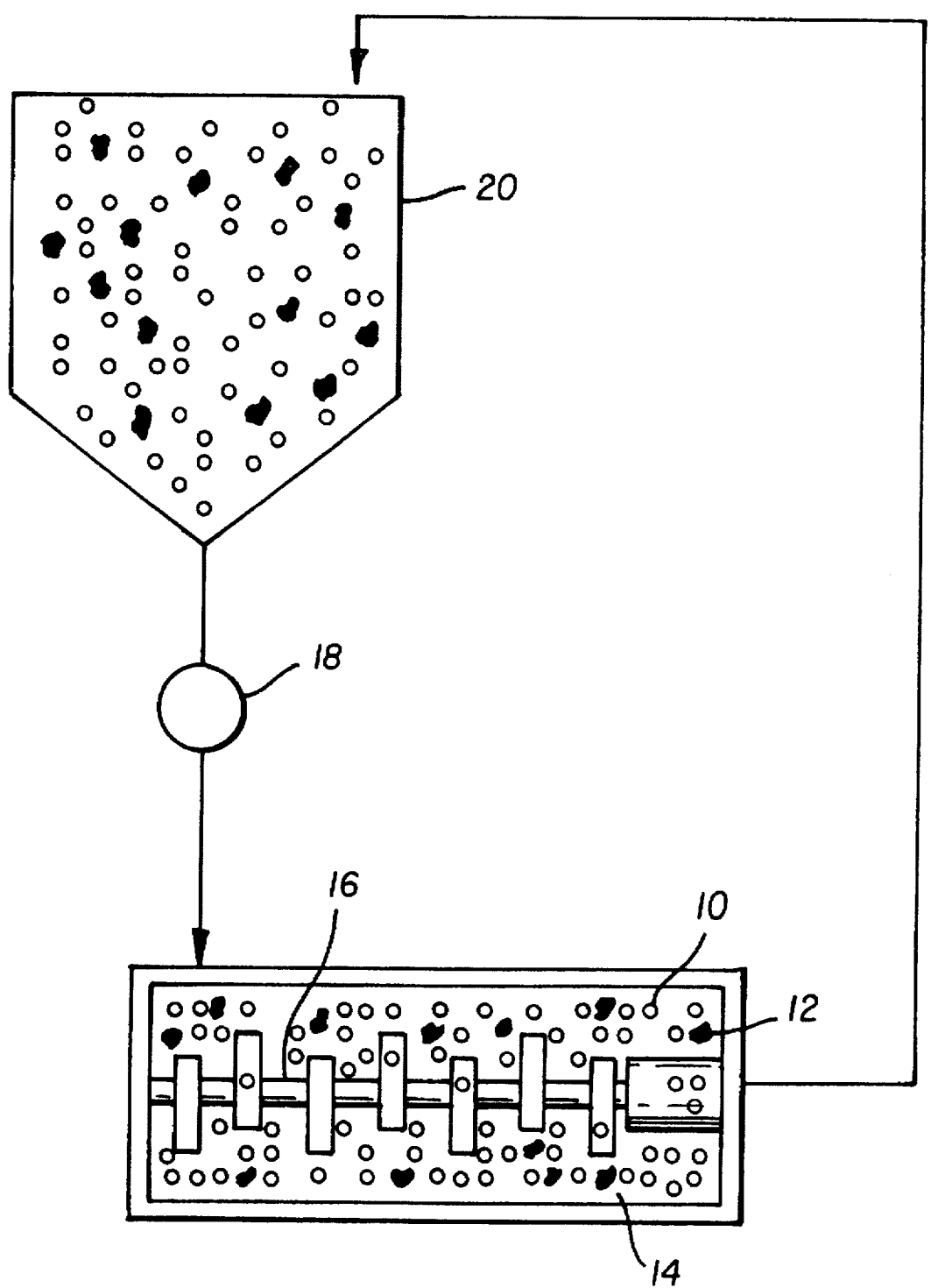
FIG. 1 is a schematic view of a preferred embodiment of a continuous grinding process in accordance with this invention.

In accordance with this invention, there is provided a continuous method of preparing submicron particles of a therapeutic or diagnostic agent. By "continuous method" it is meant that both the dispersion agent and the grinding media are continuously introduced and removed from the milling chamber. This can be contrasted to a conventional roller mill process wherein the agent and grinding media are introduced and removed from the grinding vessel in a batch process.

Liversidge et al, U.S. Pat. No. 5,145,684, and European Patent Application 498,492, describe dispersible particles consisting of a drug substance or an x-ray contrast agent having a surface modifier adsorbed on the surface thereof in an amount sufficient to maintain an effective average particle size of less than about 400 nm. The particles are prepared by dispersing a drug substance or imaging agent in a liquid dispersion medium and wet grinding in the presence of rigid grinding media. Liversidge et al do not suggest a continuous milling process wherein the grinding media is separated from the pharmaceutical agent outside the milling chamber.

Bruno et al, commonly-owned U.S. patent application Ser. No. 07/981,639 filed Nov. 25, 1992 entitled Method for Grinding Pharmaceutical Substances discloses polymeric grinding media for fine grinding pharmaceutical compositions. However, Bruno et al do not suggest a continuous process wherein the grinding media is separated from the pharmaceutical agent outside the milling chamber.

In a preferred embodiment, the grinding media can comprise particles, preferably substantially spherical in shape, e.g., beads, of a polymeric resin. However, grinding media in the form of other non-spherical shapes are expected to be useful in the practice of this invention.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polyacrylates such as polymethyl methylcrylate, polycarbonates, polyacetals, such as Delrin™, vinyl chloride polymers and copolymers, polyurethanes, polyamides, poly (tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly (glycolide) copolymers of lactides and glycolide, polyanhydrides, poly(hydroxyethyl methacrylate), poly (imino carbonates), poly(N-acylhydroxyproline)esters, poly (N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to g/cm$^3$. Higher density resins are preferred inasmuch as it is believed that these provide more efficient particle size reduction. The use of polymeric resins enable improved pH control.

Furthermore, Applicants believe that the invention can be practiced in conjunction with various inorganic grinding media prepared in the appropriate particle size. Such media include zirconium oxide, such as 95% ZrO stabilized with magnesia, zirconium silicate, glass, stainless steel, titania, alumina, and 95% ZrO stabilized with yttrium.

The media can range in size up to about 1000 microns. However, it is particularly advantageous that the invention enables the use of grinding media having a particle size of less than about 300 microns. More preferably, the media is less than about 75 microns, and, most preferably, less than about 50 microns, in size. Excellent particle size reduction has been achieved with polymeric media having a particle size of about 50 microns.

The milling process can be a dry process, e.g., a dry milling process, or a wet process, i.e., wet-grinding. In preferred embodiments, this invention is practiced in accordance with the teaching of U.S. Pat. No. 5,145,684 and European Patent Application 498,482. Thus, the wet grinding process can be practiced in conjunction with a liquid dispersion medium and surface modifier such as described in these publications. Useful liquid dispersion media include water, aqueous salt solutions, ethanol, butanol, hexane, glycol and the like. The surface modifier can be selected from known organic and inorganic pharmaceutical excipients such as described in U.S. Pat. No. 5,145,684 and can be present in an amount of 0.1–90%, preferably 1–80% by weight based on the total weight of the dry particle. A preferred surface modifier is polyvinyl pyrrolidone.

In preferred embodiments, the therapeutic or diagnostic agent can be prepared in submicron or nanoparticulate particle size, e.g., less than about 500 nm. Applicants have demonstrated that particles can be prepared having an average particle size of less than about 300 nm. In certain embodiments, particles having an average particle size of less than 100 nm have been prepared in accordance with the present invention. It was particularly surprising and unexpected that such fine particles could be prepared free of unacceptable contamination.

Grinding can take place in any suitable grinding mill. Suitable mills include an airjet mill, an attritor mill, a vibratory mill, a sand mill and a bead mill. A high energy media mill is preferred especially when the grinding media is a polymeric resin. The mill can contain a rotating shaft. This invention can also be practiced in conjunction with high speed dispersers such as a Cowles disperser, rotor-stator mixers, or other conventional mixers which can deliver high fluid velocity and high shear.

The preferred proportions of the grinding media, the therapeutic and/or diagnostic agent, the optional liquid dispersion medium, and surface modifier present in the grinding vessel can vary within wide limits and depends, for example, upon the particular therapeutic or diagnostic agent selected, the size and density of the grinding media, the type of mill selected, etc. Grinding media concentrations can range from about 10–95%, preferably 20–90% by volume depending on the application and can be optimized based on the above factors, milling performance requirements, and the flow characteristics of the combined grinding media and agent dispersion.

The attrition time can vary widely and depends primarily upon the particular therapeutic or diagnostic agent, mechanical means and residence conditions selected, the initial and desired final particle size and so forth. Residence times of less than about 8 hours are generally required using high energy dispersers and/or media mills.

The process can be carried out within a wide range of temperatures and pressures. The process preferably is carried out at a temperature below that which can cause the agent to degrade. For many agents, ambient temperatures are appropriate. Temperatures of less than about 30°–40° C. are typically preferred. Control of the temperature, e.g., by jacketing or immersion of the milling chamber in ice water are contemplated. Processing pressures from about 1 psi (0.07 kg/cm$^2$) up to about 50 psi (3.5 kg/cm$^2$) are contemplated. Processing pressures from about 10 psi (0.7 kg/cm$^2$) to about 20 psi (1.4 kg/cm$^2$) are typical.

The therapeutic or diagnostic agent and the grinding media are continuously removed from the milling chamber. Thereafter, the grinding media is separated from the milled particulate agent (in either a dry or liquid dispersion form) using conventional separation techniques, in a secondary process such as by simple filtration, sieving through a mesh filter or screen, and the like. Other separation techniques such as centrifugation may also be employed.

The invention can be practiced with a wide variety of therapeutic and diagnostic agents. In the case of dry milling, the drug substances and imaging agents must be capable of being formed into solid particles. In the case of wet milling, the drug substances and imaging agents must be poorly soluble and dispersible in at least one liquid medium. By "poorly soluble", it is meant that the therapeutic or diagnostic agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media. The therapeutic and diagnostic agents preferably are organic, crystalline materials.

Suitable therapeutic agents and classes of therapeutic agents are described in U.S. Pat. No. 5,145,684 and include 5α, 17α,-1'-(methylsulfonyl)-1'H-pregn-20-yno[3,2-c]-pyrazol-17-ol, camptothecin, piposulfam, piposulfan, naproxen and phenytoln. Other suitable drug substances include the NSAIDs described in PCT International Application PCT/US93/05082 published Dec. 23, 1993 and the anticancer agents described in European Patent Application 577,215 published Jan. 5, 1993.

Suitable diagnostic agents include derivatives of iodinated aromatic acids such as ethyl-3,5-bisacetoamido-2,4,6-triiodobenzoate (WIN 8883), ethyl(3,5-bis(acetylamino)-2, 4,6-triodobenzoyloxy) acetate (WIN 12901), ethyl-2-(his (acetylamino)-2,4,6-triodobenzoyloxy)butyrate (WIN 16318), 6-ethoxy-6-oxohexyl-3,5-bis(acetylamino)-2,4,6-triiodobenzoate (WIN 67722). Other suitable imaging agents are described in U.S. Pat. No. 5,260,478, U.S. Pat. No. 5,264,610 and European Patent Application 498,482.

In a preferred embodiment, the agent and grinding media are recirculated through the milling chamber. Examples of suitable means to effect such recirculation include conventional pumps such as peristaltic pumps, diaphragm pumps, piston pumps, centrifugal pumps and other positive displacement pumps which do not use sufficiently close tolerances to damage the grinding media. Peristaltic pumps are generally preferred.

Another variation of this process includes the use of mixed media sizes. For example, larger media may be employed in a conventional manner where such media is restricted to the milling chamber. Smaller grinding media may be continuously recirculated through the system and permitted to pass through the agitated bed of larger grinding media. In this embodiment, the smaller media is preferably between about 1 and 300 µm in mean particle size and the larger grinding media is between about 300 and 1000 µm in mean particle size.

With reference to FIG. 1, the process of this invention can be carried out as follows. The therapeutic or diagnostic agent 10 and rigid grinding media 12 are continuously introduced into milling chamber 14 which, as illustrated, contains rotating shaft 16. Peristaltic pump 18 provides the energy to recirculate the dispersion containing both the agent and grinding media through the milling chamber to holding tank 20. As opposed to conventional prior art process, there is no means for retaining the grinding media within the milling chamber, such as a screen or rotating gap separator.

The following examples further illustrate the invention.

EXAMPLE 1

Continuous Milling Process Using Fine Polymeric Media in a 0.3 Liter DynoMill

A premix dispersion was formed by combining micronized Danazol powder (2–10 µm mean size) with an aqueous PVP (average molecular weight=15,000) solution at a ratio of 5.0% Danazol, 1.5% PVP and 93.5% water. 292 grams of this premix dispersion was combined with 379.6 grams of polystyrene crosslinked with divinyl benzene (20% styrene; 80% divinylbenzene), milling media, nominal 50 micron size. This combined mixture was recirculated through a 0.3 liter DynoMill at 3200 rpm (100 cm$^3$/min) for 60 minutes (residence time). There was no means for retaining the grinding media within the milling chamber. After removal of the slurry from the milling chamber, the media was separated from the particulate Danazol using a 10 µm filter. Thereafter, the particle size was measured by CHDF. The particle size distribution showed a weight average particle size of 35 nm.

EXAMPLE 2

Continuous Milling Process Using Fine Polymeric Media in a 0.6 Liter DynoMill

A premix dispersion was formed by combining micronized Danazol powder (2–10 µm mean size) with an aqueous PVP (average MW=15,000) solution at a ratio of 5.0% Danazol, 1.5% PVP and 93.5% water. 2768 grams of this premix dispersion was combined with 3324 grams of polystyrene crosslinked with divinyl benzene (20% styrene; 80% divinyl benzene) recirculated through a 0.6 liter DynoMill at 3200 rpm (100 cm$^3$/min) for 60 minutes residence time. There was no means for retaining the grinding media within the milling chamber. After removal of the slurry from the milling chamber, the media was separated from the particle Danazol using a 10 µm filter. The particle size of this batch was not measured but microscopic examination indicated that the mean size was likely below 100 nm.

The invention has been described in detail with particular reference to certain preferred embodiments thereof, but it will be understood that variations and modifications can be effected within the spirit and scope of the invention.

We claim:

1. A continuous method of preparing submicron particles of a therapeutic or diagnostic agent, said method comprising the steps of
   a) continuously introducing said agent and rigid grinding media into a milling chamber,
   b) contacting said agent with said grinding media while in said chamber to reduce the particle size of said agent,
   c) continuously removing said agent and said grinding media from said milling chamber, and thereafter
   d) separating said agent from said grinding media.

2. The method of claim 1 wherein said media have a mean particle size of less than 1000 µm.

3. The method of claim 1 wherein said media have a mean particle size of less than 300 µm.

4. The method of claim 1 wherein said media have a mean particle size of less than 25 µm.

5. The method of claim 1 wherein said grinding media are beads of a polymeric resin.

6. The method of claim 5 wherein said polymer is polystyrene crosslinked with divinylbenzene.

7. The method of claim 5 wherein said polymer is polymethylmethacrylate.

8. The method of claim 1 wherein said therapeutic agent is Danazol.

9. The method of claim 1 wherein said diagnostic agent is selected from the group consisting of WIN 8883, WIN 12901, WIN 16318 and WIN 67722.

10. The method of claim 1 further including the step of recirculating said agent and said grinding media through said milling chamber.

11. The method of claim 1 wherein said milling chamber comprises a rotating shaft.

12. A continuous method of preparing submicron particles of a therapeutic or diagnostic agent, said method comprising the steps of
   a) continuously introducing said agent, rigid grinding media and a liquid dispersion medium into a milling chamber,
   b) wet grinding said agent with said grinding media while in said chamber to reduce the particle size of said agent,
   c) continuously removing said agent, said grinding media and said liquid dispersion medium from said milling chamber, and thereafter
   d) separating said agent from said grinding media.

* * * * *